United States Patent
Lee et al.

(10) Patent No.: US 9,969,697 B2
(45) Date of Patent: May 15, 2018

(54) 3,4-DIHYDROQUINAZOLINE DERIVATIVE AND COMBINATION COMPRISING THE SAME

(71) Applicant: UNIVERSITY-INDUSTRY COOPERATION GROUP OF KYUNG HEE UNIVERSITY, Yongin-si (KR)

(72) Inventors: Jae Yeol Lee, Seoul (KR); Kyung-Tae Lee, Seoul (KR)

(73) Assignee: UNIVERSITY-INDUSTRY COOPERATION GROUP OF KYUNG HEE UNIVERSITY, Yongin-si (KR)

(*) Notice: Subject to any disclaimer, the term of this patent is extended or adjusted under 35 U.S.C. 154(b) by 0 days. days.

(21) Appl. No.: 15/310,854

(22) PCT Filed: May 11, 2015

(86) PCT No.: PCT/KR2015/004667
§ 371 (c)(1),
(2) Date: Nov. 14, 2016

(87) PCT Pub. No.: WO2015/178608
PCT Pub. Date: Nov. 26, 2015

(65) Prior Publication Data
US 2017/0081291 A1    Mar. 23, 2017

(30) Foreign Application Priority Data
May 23, 2014 (KR) ................... 10-2014-0062507

(51) Int. Cl.
*C07D 239/84* (2006.01)
*A61K 31/498* (2006.01)
*C07D 239/74* (2006.01)
*A61K 31/506* (2006.01)
*A61K 31/517* (2006.01)
*A61K 31/5377* (2006.01)
*A61K 31/704* (2006.01)
*A61K 31/7048* (2006.01)
*A61K 33/24* (2006.01)
*A61K 45/06* (2006.01)
*A61K 47/50* (2017.01)

(52) U.S. Cl.
CPC ......... *C07D 239/84* (2013.01); *A61K 31/498* (2013.01); *A61K 31/506* (2013.01); *A61K 31/517* (2013.01); *A61K 31/5377* (2013.01); *A61K 31/704* (2013.01); *A61K 31/7048* (2013.01); *A61K 33/24* (2013.01); *A61K 45/06* (2013.01); *A61K 47/50* (2017.08); *C07D 239/74* (2013.01)

(58) Field of Classification Search
CPC .................................................... C07D 239/84
See application file for complete search history.

(56) References Cited

U.S. PATENT DOCUMENTS
2017/0081291 A1* 3/2017 Lee ................. A61K 47/48

FOREIGN PATENT DOCUMENTS

| KR | 10-2005-0084739 A | 8/2005 | |
|---|---|---|---|
| KR | 10-2008-0099108 A | 11/2008 | |
| KR | 10-2014-0017748 A | 2/2014 | |
| WO | WO2014021591 * | 2/2014 | ........ C07D 239/84 |

OTHER PUBLICATIONS

Sehyeon Cho, et al., "Three-dimensional quantitative structure-activity relationship study on anti-cancer activity of 3, 4-dihydroquinazoline derivatives against human lung cancer A549 cells", Journal of Molecular Structure, Mar. 15, 2015, pp. 294-301, vol. 1084.
Doo Li Choi, et al., "Inhibition of cellular proliferation and induction of apoptosis in human lung adenocarcinoma A549 cells by T-type calcium channel antagonist", Bioorganic & Medicinal Chemistry Letters, Mar. 15, 2014, pp. 1565-1570, vol. 24, No. 6.
William F. McCalmont, et al., "Design, synthesis, and biological evaluation of novel T-Type calcium channel antagonists", Bioorganic & Medicinal Chemistry Letters, 2004, pp. 3691-3695, vol. 14.
William F. McCalmont, et al., "Investigation into the structure-activity relationship of novel concentration dependent, dual action T-type calcium channel agonists/antagonists", Bioorganic & Medicinal Chemistry, 2005, pp. 3821-3839, vol. 13.
James Carmichael, "Evaluation of a Tetrazolium-based Semiautomated Colorimetric Assay: Assessment of Radiosensitivity", Cancer Research, Feb. 15, 1987, pp. 943-946, vol. 47.
Young H. Kim, et al., "Expression of the murine homologue of the cell cycle control protein p34$^{cdc2}$ in T lymphocytes", Jul. 1, 1992, pp. 17-23, vol. 149, No. 1.

* cited by examiner

*Primary Examiner* — Paul V Ward
(74) *Attorney, Agent, or Firm* — Sughrue Mion, PLLC

(57) ABSTRACT

A 3,4-dihydroquinazoline derivative or a pharmaceutically acceptable salt thereof and a composition containing the same are provided. The 3,4-dihydroquinazoline derivative or a pharmaceutically acceptable salt thereof show activities of blocking an intracellular influx of calcium ions acting as a secondary signal essential to the proliferation and growth of cancer cells, thereby inducing the cell cycle arrest of cancer cells, and eventually reinforcing the efficacy of existing anti-cancer drugs. A combination comprising the above compound and another anti-cancer drug is also provided.

24 Claims, No Drawings

3,4-DIHYDROQUINAZOLINE DERIVATIVE AND COMBINATION COMPRISING THE SAME

CROSS REFERENCE TO RELATED APPLICATIONS

This application is a National Stage of International Application No. PCT/KR2015/004667, filed on May 11, 2015, which claims priority from Korean Patent Application No. 10-2014-0062507, filed on May 23, 2014, the contents of all of which are incorporated herein by reference in their entirety.

TECHNICAL FIELD

The present invention relates to a 3,4-dihydroquinazoline derivative or a pharmaceutically acceptable salt thereof, which can induce the cell cycle arrest of cancer cells, thereby reinforcing the efficacy of existing anti-cancer drugs, and a combination comprising the same.

BACKGROUND ART

The Known chemotherapeutic techniques for cancer have several hindrance factors, e.g., side-effects to normal cells and tolerance to anti-cancer drugs. One method to overcome the side-effects to normal cells is known as targeted therapy which has relatively less side effects than the use of existing anti-cancer drugs. Some drugs used in the targeted therapy exhibit the effect of increasing viability in progressive colorectal cancer, breast cancer and lung cancer when being combined with other chemotherapies. However, the targeted therapy still has many problems.

For example, drugs used in the targeted therapy interfere with specific targeted molecules needed for carcinogenesis, and thus exhibit effects only for patients having the specific targeted molecules even in the same kinds of cancer. Therefore, in order to apply the targeted therapy more effectively, it is required to establish indexes to predict the effect of the targeted therapy in advance. Also, the continuous use of the targeted therapy may cause tolerance. Accordingly, there is a need to develop a novel therapeutic agent capable of raising treatment effects with overcoming the tolerance to drugs, despite of the development of the targeted therapy.

Calcium plays a critical role as an intracellular signal, and controls various cell processes, of which calcium appears to play an important role in cell growth. For example, calcium signaling is required for cell cycle progression from G1 phase to S phase during mitosis, and the depletion of intracellular calcium arrests the cell cycle in the transition of G0/G1 into S phase. Regulation of the intracellular calcium amount has been proposed to be via a T-type calcium channel. Lined with this proposition, it has recently been reported that T-type calcium channel blockers (CCBs) inhibited cellular proliferation [McCalmont, W. F., et al., *Bioorg. Med. Chem. Lett.* 2004, 14, 3691-3695; McCalmont, W. F., et al., *Bioorg. Med. Chem.* 2005, 13, 3821-38391]. Therefore, selective T-type CCBs could be another tool to treat cancer where the cell cycle is abnormal. Korean Patent Application Publication No. 10-2008-0099108 discloses a 3,4-dihydroquinazoline derivative of the following formula (A) having excellent T-type calcium channel blocking effect and anti-cancer activity.

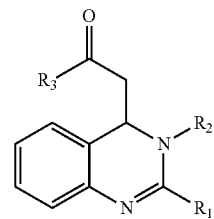

wherein,
$R_1$ is $NR_4(CH_2)_nNR_5R_6$, where $R_4$ is hydrogen or $C_1$-$C_5$ lower alkyl, n is an integer of 4 to 6, $R_5$ and $R_6$ are each independently hydrogen or $C_1$-$C_5$ lower alkyl, or taken together with the nitrogen atom to which they are attached form a 4 to 6-membered heterocycle;
$R_2$ is 4-biphenylyl;
$R_3$ is benzylamino, 4-aminobenzylamino or 4-fluorobenzenesulfoneaminobenzylamino.

The 3,4-dihydroquinazoline derivative of formula (A) just directly exhibits strong cytotoxicities against cancer cells, but has not been studied as a combination for reinforcing the efficacy of existing anti-cancer drugs.

DISCLOSURE

Technical Problem

The present inventors have endeavored to develop a T-type calcium channel blocker that can block T-type calcium channel overexpressed in cancer cells and arrest cell cycle in the transition of G0/G1 into S phase, thereby reinforcing the efficacy of existing anti-cancer drugs, and found that a 3,4-dihydroquinazoline derivative of the following formula (I) has excellent effect of cell cycle arrest.

An object of the present invention is, therefore, to provide a 3,4-dihydroquinazoline derivative or a pharmaceutically acceptable salt thereof, which can block the intracellular influx of calcium ions acting as a secondary signal essential to the proliferation and growth of cancer cells, thereby inducing the cell cycle arrest of cancer cells, and eventually reinforcing the efficacy of existing anti-cancer drugs.

Another object of the present invention is to provide a combination comprising the 3,4-dihydroquinazoline derivative of the above formula (I) or pharmaceutically acceptable salt thereof and another anti-cancer drug.

Technical Solution

One aspect of the present invention relates to a 3,4-dihydroquinazoline derivative of the following formula (I) or a pharmaceutically acceptable salt thereof:

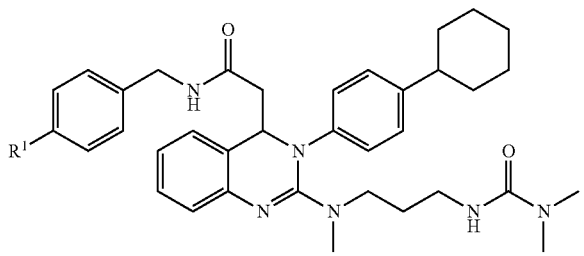

wherein,
R[1] is hydrogen, halogen or $C_1$-$C_6$ alkoxy.

The term "$C_1$-$C_6$ alkoxy" as used herein means a straight or branched alkoxy having 1 to 6 carbon atoms, which includes methoxy, ethoxy, n-propoxy and the like, but is not limited thereto.

In one embodiment of the present invention, the 3,4-dihydroquinazoline derivative is a compound wherein R[1] is halogen or $C_1$-$C_6$ alkoxy.

In the present disclosure, the pharmaceutically acceptable salt may include all non-toxic salts prepared by an inorganic acid and an organic acid, for example, hydrochloric acid, sulfuric acid, nitric acid, phosphoric acid, acetic acid, adipic acid, aspartic acid, benzoic acid, benzenesulfonic acid, citric acid, camphoric acid, camphorsulfonic acid, diphosphoric acid, ethanesulfonic acid, fumaric acid, glutaric acid, maleic acid, lactic acid, methanesulfonic acid, succinic acid, tartaric acid, picric acid, tosylic acid and the like.

The representative compounds of the present invention are selected from the following group:
4-(N-benzylacetamido)-3-(4-cyclohexylphenyl)-2-[N—(N',N'-dimethylureidopropyl)-N-methyl]amino-3,4-dihydroquinazoline (I-1);
4-[N-(4-fluorobenzyl)acetamido]-3-(4-cyclohexylphenyl)-2-[N—(N',N'-dimethylureidopropyl)-N-methyl]amino-3,4-dihydroquinazoline (I-2); and
4-[N-(4-methoxybenzyl)acetamido)-3-(4-cyclohexylphenyl)-2-[N—(N',N'-dimethylureidopropyl)-N-methyl]amino-3,4-dihydroquinazoline (I-3).

The processes for preparing the compounds according to the present invention are shown in the following Reaction Schemes 1 and 2. However, those illustrated in the following Reaction Schemes represent only typical processes used in the present invention. The manipulation order, reagents, reaction conditions, etc. may be changed without limit.

[Reaction Scheme 1]

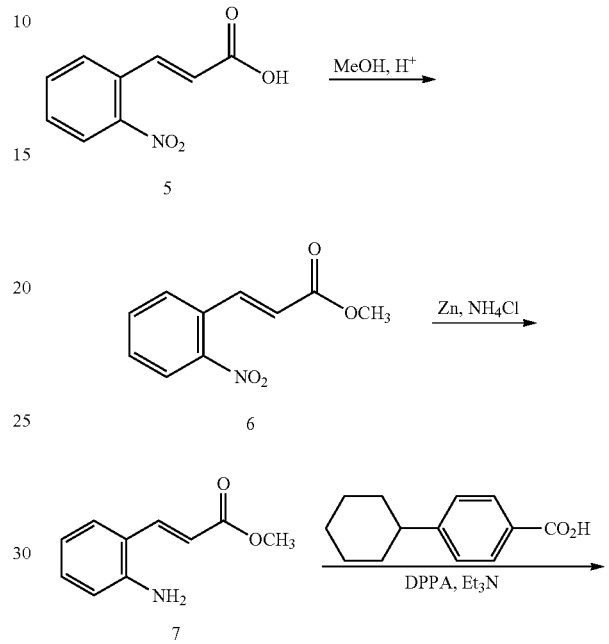

As shown in Reaction Scheme 1, 1,3-diamine compound (1) is subjected to reaction with one equivalent of di-t-butyl dicarbonate to give a Boc-protected compound (2), to which dimethylcarbamoyl chloride is added to produce compound (3) in the form of urea. Then, the Boc is removed by treatment with hydrochloric acid to give ureidoamine compound (4).

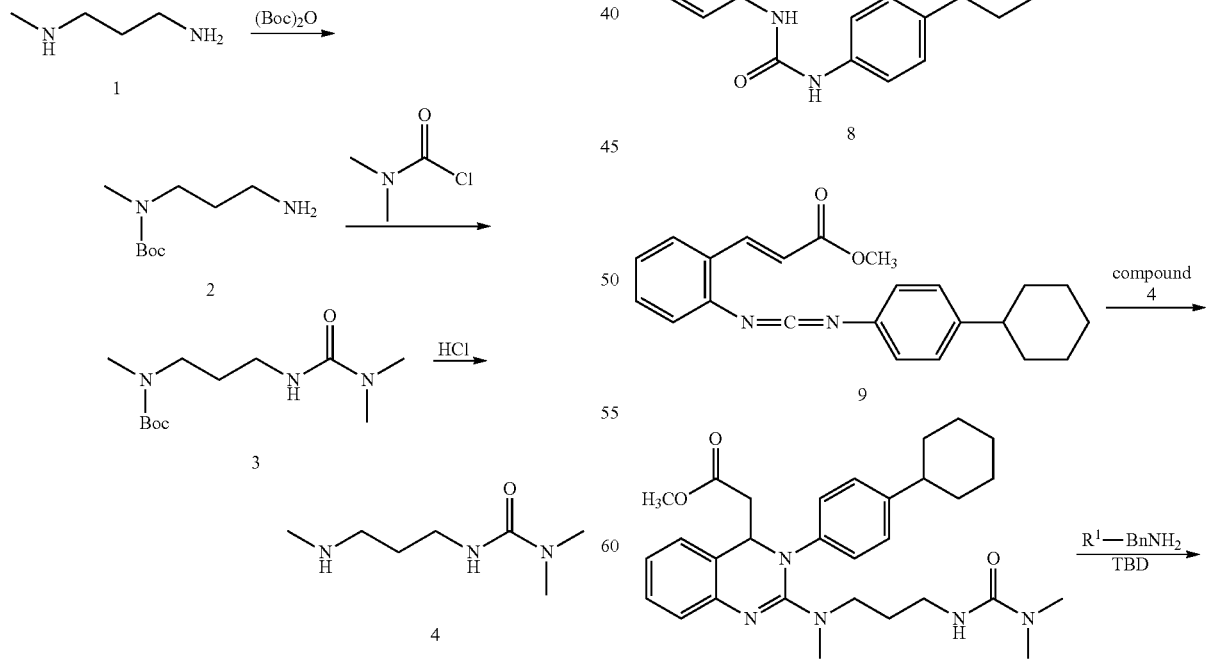

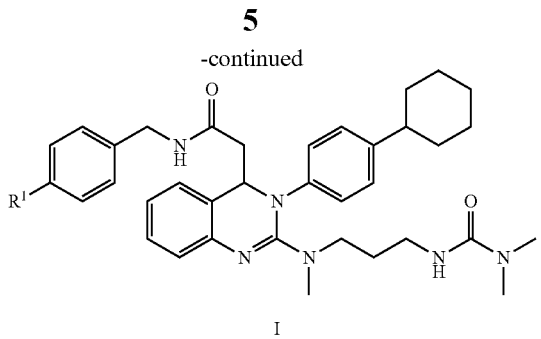

I

As shown in Reaction Scheme 2, compound (1) according to the present invention may be prepared using the compound (4) obtained according to Reaction Scheme 1.

2-Nitrocinnamic acid (5) is subjected to esterification to give methyl 2-nitrocinnamate (6) and the resultant is treated with Zn/NH$_4$Cl at 70° C. for reduction of a nitro group into an amine group to produce amine compound (7). The amine compound (7) is dissolved in a reaction solvent, to which 4-cyclohexylphenyl isocyanate obtained from reaction of 4-cyclohexylbenzoic acid and diphenylphosphoryl azide (DPPA) is added, followed by stirring at room temperature to give compound (8) in the form of urea. Then, the urea compound is subjected to dehydration using dibromotriphenylphosphine and triethylamine to give carbodiimide compound (9). The carbodiimide compound (9) is subjected to reaction with the ureidoamine compound (4) to induce nucleophilic addition in carbon existed in the center of the carbodiimide group, and then intramolecular 1,4-addition reaction is continuously carried out to produce 3,4-dihydroquinazoline (10) as an ester compound. The ester compound (10) is heated together with various benzyl amines and 1,5,7-triazabicyclo[4.4.0]dec-5-ene (TBD) without any solvent, to give the compound (1) of the present invention.

The compound of formula (I) or a pharmaceutically acceptable salt thereof according to the present invention can arrest the cell cycle of cancer cells and raise the cytotoxicity against cancer cells of existing anti-cancer drugs (See Experimental Examples presented below).

Accordingly, another aspect of the present invention relates to a combination comprising a 3,4-dihydroquinazoline derivative of formula (I) or a pharmaceutically acceptable salt thereof and another anti-cancer drug selected from the group consisting of platinum coordination complexes as anti-tumor agents, anthracyclines, topoisomerase inhibitors and tyrosine kinase inhibitors.

The combination of the present invention can be used in the treatment or prevention of cancers such as lung cancer, sarcoma, malignant melanoma, pleural mesothelioma, bladder cancer, prostate cancer, pancreatic cancer, stomach cancer, ovarian cancer, liver cancer, breast cancer, colon cancer, kidney cancer, esophageal cancer, adrenal cancer, salivary gland cancer, head and neck cancer, cervical cancer, mesothelioma, leukemia and lymphoma.

Specifically, one embodiment of the present invention relates to a combination for treatment or prevention of stomach cancer, bladder cancer, lung cancer, pancreatic cancer or colon cancer, comprising a 3,4-dihydroquinazoline derivative of formula (I) or a pharmaceutically acceptable salt thereof and a platinum coordination complex for anti-tumor.

The platinum coordination complex for anti-tumor may include cisplatin, oxaliplatin, carboplatin, BBR3464, satraplatin, tetraplatin, omiplatin or iproplatin, particularly cisplatin, but is not limited thereto.

Other embodiment of the present invention relates to a combination for treatment or prevention of stomach cancer, lung cancer or breast cancer, comprising a 3,4-dihydroquinazoline derivative of formula (I) or a pharmaceutically acceptable salt thereof and an anthracycline.

The anthracycline may include daunorubicin, doxocubicin, epirubicin, idarubicin, mitoxantrone, pixantrone or valrubicin, particularly doxorubicin, but is not limited thereto.

Another embodiment of the present invention relates to a combination for treatment or prevention of stomach cancer, lung cancer or colon cancer, comprising a 3,4-dihydroquinazoline derivative of formula (I) or a pharmaceutically acceptable salt thereof and a topoisomerase inhibitor.

The topoisomerase inhibitor may include topotecan, SN-38, irinotecan, camptothecin, rubitecan, etoposide or teniposide, particularly etoposide, but is not limited thereto.

Still another embodiment of the present invention relates to a combination for treatment or prevention of liver cancer, lung cancer or pancreatic cancer, comprising a 3,4-dihydroquinazoline derivative of formula (I) or a pharmaceutically acceptable salt thereof and a tyrosine kinase inhibitor.

The tyrosine kinase inhibitor may include erlotinib, sorafenib, axitinib, bosutinib, cediranib, dasatinib, gefitinib, imatinib, canertinib, lapatinib, lestaurtinib, nitotinib, semaxanib, sunitinib or vandetanib, particularly erlotinib, gefitinib or imatinib, but is not limited thereto.

The combination according to the present invention may be administered via oral (e.g., taking through mouth or inhalation) or parenteral (e.g., injection, deposition, implantation or suppositories) routes. The injection may be, for example, intravenous, subcutaneous, intramuscular or intraperitoneal. The combination of the present invention may be formulated in the form of tablets, capsules, granules, fine subtilae, powders, sublingual tablets, suppositories, ointments, injection solutions, emulsions, suspensions, syrups, aerosols, etc., depending on the route of administration. The above various forms of the combination of the present invention may be prepared using a pharmaceutically acceptable carrier which is conventionally used in the art by the known methods. Examples of the pharmaceutically acceptable carrier may include excipients, binders, disintegrating agents, lubricants, preservatives, antioxidants, isotonic agents, buffering agents, coating agents, sweeteners, solubilizers, bases, dispersing agents, wetting agents, suspending agents, stabilizers, coloring agents and the like.

The combination of the present invention contains 0.01 to 95 wt % of the compound of the present invention or a pharmaceutically acceptable salt thereof and another anti-cancer drug, although varied depending on the types of the formulations.

The specific dosage of the combination of the present invention may be determined depending on the kinds, weight, sex, severity of disease of mammals to be treated, including a human, the physician's decision and the like. Preferably, a daily dosage for oral administration may range from 0.01 to 50 mg of an active ingredient per kg of body weight, while a daily dosage for parenteral administration may range from 0.01 to 10 mg of an active ingredient per kg of body weight. The total daily dosage may be administered in a single dose or divided doses, depending on the severity of diseases, the physician's decision and other conditions.

Also, the 3,4-dihydroquinazoline derivative or a pharmaceutically acceptable salt thereof of the present invention and another anti-cancer drug may be each provided as individual formulations for administration at the same time or different times. Preferably, the 3,4-dihydroquinazoline derivative and another anti-cancer drug are provided as individual formulations for administration at different times. In the case of individual administration at different times, any one of the 3,4-dihydroquinazoline derivative and another anti-cancer drug may be first administered. Also, two kinds of drugs may be administered at the same date or different dates, and the same schedule or different schedules of administration may be applied during treatment cycle.

The combination of the present invention contains all ingredients (drugs) in a single pharmaceutically acceptable formulation. Also, these ingredients may be individually formulated and then administered in a combination thereof. Formulations well known to a person having ordinary skill in the art may be applied in the present invention. In addition, the drugs of the combination may be administered via routes different from each other. For example, one of drugs may be formulated in the form of being suitable for oral administration, e.g., tablets and capsules, and the others may be formulated in the form of being suitable for parenteral injection (intravenous, subcutaneous, intramuscular, intravascular or infusion), e.g., sterilized solutions, suspensions or emulsions. Also, both of two drugs may be administered via the same route. The selection of formulations suitable to be used in the present invention may be conventionally determined by a person having ordinary skill in the art depending on administration methods and the solubility of ingredients.

The accurate dosage of ingredients forming the combination may be determined depending on specific formulations, administration methods, specific parts to be treated, patients and tumors. Also, other factors such as age, weight, sex, dietary, administration time, excretion rate, the condition of patient, combination of drugs, the sensitivity of response and severity of disease should be considered. Administration may be carried out simultaneously or periodically within maximum tolerance dosage.

Advantageous Effects

The 3,4-dihydroquinazoline derivative of the present invention can block the intracellular influx of calcium ions acting as a secondary signal essential to the proliferation and growth of cancer cells, thereby inducing the cell cycle arrest of cancer cells, and eventually providing strong synergism in anti-cancer activity when the derivative is administered in a combination with an existing anti-cancer drug, as compared with single administration of only the existing anti-cancer drug.

BEST MODE

The present invention is further illustrated by the following examples, which are not to be construed to limit the scope of the invention.

Preparation Example 1: Synthesis of t-butyl-N-(3-aminopropyl)-N-methylcarbamate (2)

N-methyl-1,3-diaminopropane (1) (3.26 g, 37.03 mmol) was added in methanol (100 ml), to which 35% HCl solution was slowly added at 0° C., followed by stirring. After stirring the reaction solution for 30 minutes at room temperature, di-t-butyl-dicarbonate (10.51 g, 48.14 mmol) was slowly added at −10° C. After concentration under reduced pressure, the resultant was subjected to alkalinization with 10% aqueous sodium hydroxide solution, extracted with dichloromethane, and dried over anhydrous magnesium sulfate. The residue was concentrated under reduced pressure and was subjected to silica gel column chromatography (eluent:dichloromethane:methanol:ammonia water=100:9:1, v/v/v) to give the target compound (2).

Yield: 3.03 g (43%)

$^1$H NMR (400 MHz, CDCl$_3$) δ 3.29 (2H, br, —CH$_2$—NH$_2$), 2.83 (3H, s, —N—CH$_3$), 2.69 (2H, t, J=6 Hz, —N—CH—CH$_2$—), 1.64 (2H, m, —CH$_2$—C$_2$—CH$_2$—), 1.46 (9H, s, (CH$_3$)$_3$—O—C=O), 1.38 (2H, s, —CH$_2$—CH$_2$—NH$_2$).

Preparation Example 2: Synthesis of t-butyl-N-[3-(N',N'-dimethylureido-propyl)]-N-methylcarbamate (3)

t-Butyl-N-(3-aminopropyl)-N-methylcarbamate (2) (2.19 g, 11.63 mmol) was added in anhydrous dichloromethane (100 ml). To the resulting mixture, triethylamine (1.77 g, 17.45 mmol) was added. Then, dimethylcarbamoyl chloride (1.87 g, 17.45 mmol) was slowly added at −10° C., followed by stirring for 4 hours. After concentration under reduced pressure, the resultant was extracted with ethyl acetate and dried over anhydrous magnesium sulfate. The residue was concentrated under reduced pressure and was subjected to silica gel column chromatography (eluent:ethyl acetate:hexane=15:1, v/v) to give the target compound (3).

Yield: 2.78 g (92%)

$^1$H NMR (400 MHz, CDCl$_3$) δ 5.85 (1H, br, —CH$_2$—NH—C=O), 3.34 (2H, s, —N(CH$_3$)—CH$_2$—CH$_2$—), 3.19 (2H, s, —CH$_2$—CH$_2$—NH—), 2.92 (6H, s, —N—(CH$_3$)$_2$), 2.81 (3H, s, —N(CH$_3$)—CH$_2$—), 1.63 (2H, m, —CH$_2$—CH$_2$—CH$_2$—), 1.46 (9H, s, (CH$_3$)$_3$—O—C=O).

Preparation Example 3: Synthesis of N,N-dimethyl-N'-(3-methylaminopropyl)urea (4)

t-Butyl-N-[3-(N',N'-dimethylureido-propyl)]-N-methylcarbamate (3) (2.7 g, 10.41 mmol) was added in methanol (100 ml), to which 2 equivalents-volume (41.61 ml) of 0.5M hydrogen chloride diluted in methanol was slowly added at 0° C., followed by stirring. After concentration under reduced pressure, the resultant was subjected to alkalinization with 10% aqueous sodium hydroxide solution, extracted with dichloromethane, and dried over anhydrous magnesium sulfate. The residue was concentrated under reduced pressure to give the target compound (4).

Yield: 1.04 g (63%)

$^1$H NMR (400 MHz, CDCl$_3$) δ 5.95 (1H, br, —CH$_2$—NH—C=O), 3.33 (2H, q, J=6 Hz, —CH$_2$—NH—C=O), 3.05 (1H, br, CH$_3$—NH—CH$_2$), 2.89 (6H, s, —N—(CH$_3$)$_2$), 2.74 (2H, t, J=6 Hz, CH$_3$—NH—CH$_2$—C$_2$—), 2.45 (3H, s, CH$_3$—NH—CH$_2$—), 1.72 (2H, m, —CH$_2$—CH$_2$—CH$_2$—).

Preparation Example 4: Synthesis of methyl 2-nitrocinnamate (6)

2-Nitrocinnamic acid (3.00 g, 15.53 mmol) was added in methanol (100 ml), to which saturated sulfuric acid (0.25 ml) was added, followed by stirring with reflux overnight. The reaction mixture was concentrated, then it was diluted with ethylacetate (150 ml) and washed with water (100 ml). The organic layer was dried over anhydrous magnesium sulfate and concentrated under reduced pressure to give the target compound (6). The resultant was used as it is in the next reaction without particular purification.

Yield: 3.21 g (99%)

¹H NMR (400 MHz, CDCl₃) δ 8.14 (1H, d, J=16 Hz, —C—CH═CH—), 8.09-7.58 (4H, m, aromatic), 6.39 (1H, d, J=16 Hz, —C—CH═CH—), 3.86 (3H, s, —OCH₃).

Preparation Example 5: Synthesis of methyl 2-aminocinnamate (7)

Methyl 2-nitrocinnamate (6) (3.21 g, 15.53 mmol), zinc (5.05 g, 77.65 mmol) and an excessive amount of NH₄Cl were added in ethyl acetate (100 ml), and the reaction mixture was heated to 70° C. for 1 hour. After the reaction was completed, the reaction mixture was cooled down to room temperature, and an aqueous solution of sodium hydrogen carbonate was added thereto. The mixture was filtered through Celite 545 (Samchun Chemical) to remove solid materials, and the crude product was extracted with ethyl acetate. The organic layer is collected, dried over anhydrous magnesium sulfate and concentrated under reduced pressure to give the target compound (7) as a yellow crystal.

Yield: 2.62 g (95%)
¹H NMR (400 MHz, CDCl₃) δ 7.89 (1H, d, J=24.0 Hz, —C—CH═CH—), 7.44-6.76 (4H, m, aromatic), 6.39 (1H, d, J=24.0 Hz, —C—CH═CH—), 3.83 (3H, s, —OCH₃).

Preparation Example 6: Synthesis of methyl (E)-2-[3-(4-cyclohexylphenyl)ureido]cinnamate (8)

To a mixture obtained by adding 4-cyclohexylbenzoic acid (3.64 g, 17.83 mmol) in toluene (100 diphenylphosphoryl azide (DPPA, 5.89 g, 21.40 mmol) and triethylamine (3.61 g, 35.67 mmol) were added at room temperature and stirred for 3 hours, followed by stirring at 100° C. for 3 hours. The reaction mixture was cooled down to room temperature, and methyl 2-aminocinnamate (7) (3.16 g, 17.83 mmol) was added thereto, followed by stirring for 12 hours. After adding methanol to the mixture, the precipitated product was filtered and washed with methanol to give the target compound (8) as a white crystal.

Yield: 4.98 g (73%)
¹H NMR (400 MHz, CDCl₃) δ 7.94 (1H, d, J=16 Hz, —C—CH═CH—), 7.75-7.15 (10H, in, aromatic and Ph-NH—CO—NH-Ph-), 6.40 (1H, d, J=16 Hz, —C—CH═CH—), 3.77 (3H, s, —OCH₃), 2.46 (1H, m, -Ph-CH(CH₂)₂—), 1.76 (4H, m, -Ph-CH(CH₂)₂—), 1.44-1.34 (4H, m, —(CH₂)₂—CH₂), 1.30-1.23 (2H, m, —(CH₂)₂—CH₂).

Preparation Example 7: Synthesis of methyl (E)-2-(4-cyclohexylphenyliminomethyleneamino)cinnamate (9)

Methyl (E)-2-[3-(4-cyclohexylphenyl)ureido]cinnamate (8) (2.78 g, 7.34 mmol) and triethylamine (2.23 g, 22.01 mmol) were added in dichloromethane (100 ml) to give a mixture, to which dibromotriphenylphosphine (4.65 g, 11.01 mmol) was slowly added at 0° C. The reaction mixture was stirred for 1 hour at 0° C., extracted with dichloromethane. The organic layer is collected, dried over anhydrous magnesium sulfate and concentrated under reduced pressure. After adding methanol to the mixture, the precipitated product was filtered and washed with methanol to give the target compound (9) as a white crystal.

Yield: 2.12 g (80%)
¹H NMR (400 MHz, CDCl₃) δ 8.17 (1H, d, J=16 Hz, —C—CH═CH—), 7.61-7.12 (8H, m, aromatic), 6.53 (1H, d, J=16 Hz, —C—CH═CH—), 3.83 (3H, s, —OCH₃), 2.51 (1H, m, -Ph-CH(CH₂)₂—), 1.88 (4H, s, -Ph-CH(CH₂)₂—), 1.46-1.35 (4H, m, —(CH₂)₂—CH₂), 1.31-1.24 (2H, m, —(CH₂)₂—CH₂).

Preparation Example 8: Synthesis of 4-[methoxycarbonylmethyl]-3-(4-cyclohexylphenyl)-2-[N—(N', N'-dimethylureidopropyl)-N-methyl]amino-3,4-dihydroquinazolin (10)

To a solution of methyl (E)-2-(4-cyclohexylphenyliminomethyleneamino)cinnamate (9) (0.61 g, 1.69 mmol) in toluene (50 ml), N,N-dimethyl-N'-(3-methylaminopropyl) urea (4) (0.27 g, 1.69 mmol) was added and stirred for 2 hours, followed by concentration under reduced pressure. After extraction with dichloromethane, the organic layer was dried over anhydrous magnesium sulfate and concentrated under reduced pressure. The residue was subjected to silica gel column chromatography (eluent: dichloromethane:methanol:ammonia water=100:9:1, v/v/v) to give the target compound (10).

Yield: 0.87 g (99%)
¹H NMR (400 MHz, CDCl₃) δ 7.28-6.92 (8H, m, aromatic), 6.37 (1H, br, —CH₂—NH—C═O), 5.10 (1H, dd, J=4.8 Hz and 10.4 Hz, —CH₂—CH—N), 4.09-1.21 (31H, m).

Example 1: Preparation of 4-[N-benzylacetamido]-3-(4-cyclohexylphenyl)-2-[N—(N',N'-dimethylureidopropyl)-N-methyl]amino-3,4-dihydroquinazolin (I-1)

4-[Methoxycarbonylmethyl]amino-3-(4-cyclohexylphenyl)-2-[N',N'-dimethylureidopropyl)-N-methyl]amino-3,4-dihydroquinazolin (10) (0.11 g, 0.21 mmol) and 0.3 equivalent of 1,5,7-triazabicyclo[4.4.0]dec-5-ene (TBD) (89 mg, 0.06 mmol) were added in 2.4 equivalents-volume of 4-benzylamine (0.06 ml), followed by stirring for 12 hours at 40° C. The reaction mixture was concentrated under reduced pressure, and the concentrate was subjected to silica gel column chromatography (eluent: dichloromethane:methanol:ammonia water=100:9:1, v/v/v) to give the target compound (I-1).

Yield: 90%,
¹H NMR (400 MHz, CDCl₃) δ 7.22-6.83 (13H, m), 5.81 (1H, br), 5.12 (1H, dd), 4.42 (1H, dd), 4.31 (1H, dd), 4.12 (1H, br), 3.31-1.02 (28H, m).

Example 2: Preparation of 4-[N-(4-fluorobenzyl)acetamido]-3-(4-cyclohexylphenyl)-2-[N—(N',N'-dimethylureidopropyl)-N-methyl]amino-3,4-dihydroquinazolin (I-2)

4-[Methoxycarbonylmethyl]-3-(4-cyclohexylphenyl)-2-[N—(N',N'-dimethylureidopropyl)-N-methyl]amino-3,4-dihydroquinazolin (10) (0.11 g, 0.21 mmol) and 0.3 equivalents of 1,5,7-triazabicyclo[4.4.0]dec-5-ene(TBD) (89 mg, 0.06 mmol) were added in 2.4 equivalents-volume of 4-fluorobenzylamine (0.06 ml), followed by stirring for 12 hours at 40° C. The reaction mixture was concentrated under reduced pressure, and the concentrate was subjected to silica gel column chromatography (eluent: dichloromethane:methanol:ammonia water=100:9:1, v/v/v) to give the target compound (I-2).

Yield: 96%.
¹H NMR (400 MHz, CDCl₃) δ 7.69 (1H, br), 7.30-6.83 (12H, m), 5.76 (1H, br), 5.12 (1H, dd), 4.39 (1H, dd), 4.28 (1H, dd), 3.28-1.13 (31H, m).

Example 3: Preparation of 4-[N-(4-methoxybenzyl) acetamido]-3-(4-cyclohexylphenyl)-2-N—[N',N'-dimethylureidopropyl)-N-methyl]amino-3,4-dihydroquinazolin (I-3)

4-[methoxycarbonylmethyl]-3-(4-cyclohexylphenyl)-2-[N—(N',N'-dimethylureidopropyl)-N-methyl]amino-3,4-dihydroquinazolin (10) (0.11 g, 0.21 mmol) and 0.3 equivalents of 1,5,7-triazabicyclo[4.4.0]dec-5-ene(TBD) (89 mg, 0.06 mmol) were added to 2.4 equivalents-volume of 4-methoxybenzylamine (0.06 ml), followed by stirring for 12 hours at 40° C. The reaction mixture was concentrated under reduced pressure, and the concentrate was subjected to silica gel column chromatography (eluent:dichloromethane:methanol:ammonia water=100:9:1, v/v/v) to give the target compound (I-3).

Yield: 97%, $^1$H NMR (400 MHz, CDCl$_3$) δ 7.67 (1H, br), 7.23-6.68 (12H, m), 6.02 (1H, br), 5.13 (1H, dd), 4.43 (1H, dd), 4.20 (1H, dd), 3.67 (3H, s), 3.25-1.18 (31H, m).

Experiment Example 1: Methods for Culturing HEK293 Cells and Measuring T-type Calcium Channel Activity Using an Electrophysiological Method HEK293 cells were cultured in Dulbecco's modified Eagle's medium (DMEM) supplemented with 10% fetal bovine serum (FBS) and 1% penicillin/streptomycin (v/v) in 36.5° C. humidified incubator (95% air-5% CO$_2$). The culture medium was replaced with a fresh medium every 3 to 4 days, and the cultured cells were subjected to sub-culture every week. At this time, the culture solution was treated with G-418 (0.5 mg/mL) solution so that only HEK293 cells expressing α$_{1G}$ T-type calcium channel can grow. The cells used for T-type calcium channel activity assay were cultured on a cover slip coated with poly-L-lysine (0.5 mg/mL) whenever sub-cultured, and their calcium channel activity was recorded 2 to 7 days after the cultivation. Current of the T-type calcium channel at a single cell level was measured according to an electrophysiological whole-cell patch-clamp method using EPC-9 amplifier (HEKA, Germany). At this time, a cell exterior solution [NaCl 140 mM, CaCl$_2$ 2 mM, and HEPES 10 mM (pH 7.4)] and a cell interior solution [KCl 130 mM, HEPES 10 mM, EGTA 11 mM, and MgATP 5 mM (pH 7.4)] were employed. Inward current caused by the T-type calcium channel activation which occurred when the cells were converted into a whole-cell recording mode by stabbing a microglass electrode having 3-4 MΩ resistance which was filled with the cell interior solution into a single cell and depolarized at −30 mV (50 ms duration period) every 10 s with fixing membrane potential to −100 mV was measured according to a T-type calcium Channel activity protocol activated at low voltage.

Experiment Example 2: Method for Assessing Cytotoxicity on Cancer Cells

A549 cell line (human lung cancer) and PANC-1 cell line (human pancreatic cancer) were obtained from Korean Cell Line Bank (KCLB). The cells were cultured in RPMI 1640 medium supplemented with 10% fetal bovine serum (FBS) being heated and inactivated, penicillin (100 units/ml) and streptomycin sulfate (100 units/ml) under the condition of 37° C. and 5% CO$_2$.

In order to confirm the cytotoxicity of drugs, an MTT (3-(4,5-dimethylthiazol-2-yl)-2,5-diphenyltetrazolium bromide) assay was conducted as follows [See Armichael et al., Evaluation of a tetrazolium-based semiautomated colorimetric assay: assessment of chemisensitivity testing. *Cancer Research*, 47, pp. 944-946, 1987]. The MTT assay is based on the reduction of water-soluble MTT (tetrazolium salt, yellow) which can be absorbed in living cells to its water-insoluble formazan crystals (purple) by activity of oxidoreductase enzymes of mitochondria. That is, when the number of viable cells is more, the formation of formazan crystals increases and the value of absorbance becomes higher.

Each of the cultured cancer cells was inoculated in a 96-well plate (5×10$^4$ cells/well) and cultured in RPMI medium (100 μl) containing 5% FBS. In 48 hours after the treatment of drugs (200, 100, 50, 25, 12.5, 6.25, 3.125 μM), 20 μl of an MTT solution (5.0 mg/ml) was added to each well, followed by further incubation for 4 hours. The supernatant of the plate was collected, and formazan crystals formed by MTT in the cells were added in 200 μl of DMSO to dissolve the precipitate. The OD value was measured at 540 nm using microplate reader (Molecular Devices).

Experiment Example 3: Method for Assessing Cell Cycle Arrest of Cancer Cells

Experiment Example 3-1: PI Staining

To measure the inviability of cancer cells quantitatively, the cell cycle thereof was analyzed through flow cytometry as follows, in accordance with the method given in the document [See Kim, Y. H. et al., Expression of the murine homologue of the cell cycle control protein p32cdc2 in T lymphocytes. *Journal of Immunology*, 149, pp. 17-23, 1992].

A549 cells (1.0×10$^5$ cell/well) treated with drugs for 48 hours were immobilized in 70% ice-cold ethanol and left overnight at 4° C. After adding ribonuclease (2.5 μg/ml) and propidium iodide (50 μg/ml) together with 500 μl of PBS, the cells were left for 30 minutes in the dark at room temperature, followed by analyzing cell cycle within 1 hour using FACScan flow cytometer (Becton Dickinson Co, Heidelberg, Germany).

Experiment Example 3-2: Annexin V-FITC/PI Double Staining Assay

Cell death include the event that phosphatidylserine translocated to the surface of cell membrane is bound to Annexin V-FITC to express fluorochromes. Cells were treated with drugs, harvested, washed with ice-cold PBS twice, and supplied with 100 μl of Annexin V binding buffer (10 nM 4-(2-hydroxyethyl)piperazine-1-ethanesulfonic acid (HEPES)/NaOH, 140 mM NaCl, 2.5 mM CaCl$_2$, pH 7.4). Thereto, 5 μl of FITC-conjugated Annexin V and PI (50 μg/ml) were added. The mixture was left for 30 minutes in the dark at room temperature, followed by analysis within 1 hour using FACScan flow cytometer (Becton Dickinson Co, Heidelberg, Germany).

Experiment Example 4: Assessment of Combination Index (CI)

Combination index (CI) mathematically expresses the cytotoxicity on cancer cells or growth inhibition of cancer cells through relative comparison after treating drugs alone or in a combination. The CI is the quantitative concept introduced by Paul Talalay and Ting-Chao Chou and was calculated using CalcuSyn software. The effect of combination treatment according to the values of CI was defined as follows.

CI<0.9: synergism
CI=0.9-1.1: additivity
CI>1.1: antagonism

The T-type calcium channel blocking effects and growth inhibition effects against lung cancer cells (A549) of the compounds according to the present invention, which are analyzed in the Experiment Examples, are shown in Table 1.

TABLE 1

| Compound | T-type calcium channel blocking effect (IC$_{50}$: µM) | Cytotoxicity A549 (IC$_{50}$: µM) | 24 Hours | | | | 48 Hours | | | |
|---|---|---|---|---|---|---|---|---|---|---|
| | | | SubG1 | G0/G1 | S | G2/M | SubG1 | G0/G1 | S | G2/M |
| Control Group | — | — | 7.8 | 53.1 | 17.6 | 21.6 | 4.9 | 57.8 | 12.0 | 25.4 |
| I-1 | 0.39 ± 0.11 | 12.2 | 3.6 | 65.5 | 16.1 | 14.8 | 6.6 | 59.9 | 15.8 | 17.7 |
| I-2 | 0.89 ± 0.06 | 7.3 | 4.7 | 63.6 | 12.4 | 19.3 | 3.5 | 67.7 | 14.5 | 14.3 |
| I-3 | ND | 8.0 | 3.8 | 71.2 | 9.4 | 15.6 | 4.0 | 67.2 | 16.3 | 12.4 |
| Mibefradil | 1.34 ± 0.49 | 24.9 | 5.3 | 67.3 | 10.4 | 17.1 | 10.3 | 55.9 | 18.8 | 14.9 |

As shown in Table 1, the 3,4-dihydroquinazoline derivative according to the present invention exhibited good effects in terms of blocking T-type calcium channel overexpressed in cancer cells and arresting the cell cycle in the transition of G0/G1 into S phase, as compared with the control group and the positive control material (mibefradil).

As presented in the Experiment Examples, lung cancer cells (A549) were treated for 48 hours with a combination of compound (I-2) according to the present invention and Cisplatin as the existing anti-cancer drug, then the cell cycle thereof was analyzed by PI staining and the values of CI were calculated based on the values of SubG1 (i.e., cell death). The results are shown in Table 2.

TABLE 2

| | SubG1 | G0/G1 | S | G2/M | CI |
|---|---|---|---|---|---|
| Control Group | 1.7 | 68.7 | 16.1 | 12.2 | |
| Cisplatin (20 µM) | 10.5 | 9.0 | 13.1 | 67.5 | |
| Cisplatin (30 µM) | 17.0 | 14.0 | 15.8 | 52.9 | |
| I-2 (10 µM) | 7.6 | 79.1 | 2.4 | 10.9 | |
| Cisplatin (20 µM) + I-2 (10 µM) | 29.1 | 48.1 | 10.4 | 12.5 | 0.577 |
| Cisplatin (30 µM) + I-2 (10 µM) | 52.3 | 32.4 | 6.1 | 9.4 | 0.371 |

As presented in the Experiment Examples, pancreatic cancer cells (PANC-1) were treated for 48 hours with a combination of compound (I-2) according to the present invention and Cisplatin as the existing anti-cancer drug, then the cell cycle thereof was analyzed by PI staining and the values of CI were calculated based on the values of SubG1 (i.e., cell death). The results are shown in Table 3.

TABLE 3

| | SubG1 | G0/G1 | S | G2/M | CI |
|---|---|---|---|---|---|
| Control Group | 1.8 | 37.2 | 8.4 | 36.5 | |
| Cisplatin (30 µM) | 9.3 | 42 | 9.4 | 29.4 | |

TABLE 3-continued

| | SubG1 | G0/G1 | S | G2/M | CI |
|---|---|---|---|---|---|
| I-2 (2.5 µM) | 2.5 | 44.7 | 7.2 | 35 | |
| Cisplatin + I-2 | 25.2 | 35.5 | 7.7 | 24.9 | 0.755 |

As presented in the Experiment Examples, lung cancer cells (A549) were treated for 48 hours with a combination of compound (I-2) according to the present invention and Etoposide as the existing anti-cancer drug, then the cell cycle thereof was analyzed by PI staining and the values of CI were calculated based on the values of SubG1 (i.e., cell death). The results are shown in Table 4.

TABLE 4

| | SubG1 | G0/G1 | S | G2/M | CI |
|---|---|---|---|---|---|
| Control Group | 0.9 | 61.1 | 12.4 | 24.8 | |
| Etoposide (50 µM) | 33.0 | 36.0 | 12.3 | 18.9 | |
| I-2 (10 µM) | 4.0 | 77.4 | 5.4 | 13.3 | |
| Etoposide + I-2 | 83.1 | 7.9 | 6.2 | 3.2 | 0.166 |

As presented in the Experiment Examples, lung cancer cells (A549) were treated for 48 hours with a combination of compound (I-2) according to the present invention and Erlotinib, Gefitinib, Imatinib or Doxorubicin as the existing anti-cancer drug, then the cell cycle thereof was analyzed by PI staining and the values of CI were calculated based on the values of SubG1 (i.e., cell death). The results are shown in Table 5.

TABLE 5

| | SubG1 | G0/G1 | S | G2/M | CI |
|---|---|---|---|---|---|
| Control Group | 1.8 | 62.9 | 15.1 | 20.9 | |
| I-2 (10 µM) | 3.7 | 76.8 | 7.6 | 12.1 | |
| erlotinib (150 µM) | 9.6 | 70.6 | 7.2 | 12.9 | |
| Gefitinib (40 µM) | 11.6 | 72.7 | 4 | 11.8 | |
| Imatinib (100 µM) | 2.9 | 72.4 | 10.7 | 14.4 | |
| Doxorubicin (10 µM) | 33.5 | 36.7 | 11.9 | 18.3 | |
| erlotinib + I-2 | 97.9 | 1.9 | 0.2 | 0.1 | 0.271 |
| Gefitinib + I-2 | 96 | 3.7 | 0.3 | 0.1 | 0.150 |
| Imatinib + I-2 | 86.7 | 11.4 | 1.4 | 0.9 | 0.493 |
| Doxorubicin + I-2 | 72.1 | 14.7 | 4.9 | 8.4 | 0.101 |

As presented in the Experiment Examples, lung cancer cells (A549) were treated for 48 hours with a combination of compound (I-3) according to the present invention and Erlotinib, Gefitinib, Imatinib or Doxorubicin as the existing anti-cancer drug, then the cell cycle thereof was analyzed by PI staining and the values of CI were calculated based on the values of SubG1 (i.e., cell death). The results are shown in Table 6.

TABLE 6

|  | SubG1 | G0/G1 | S | G2/M | CI |
|---|---|---|---|---|---|
| Control Group | 1.8 | 62.9 | 15.1 | 20.9 | |
| I-3 (10 μM) | 3.7 | 76.8 | 7.6 | 12.1 | |
| erlotinib (300 μM) | 70.3 | 27.7 | 1 | 1.2 | |
| Gefitinib (40 μM) | 11.6 | 72.7 | 4 | 11.8 | |
| Imatinib (100 μM) | 2.9 | 72.4 | 10.7 | 14.4 | |
| Doxorubicin (10 μM) | 33.5 | 36.7 | 11.9 | 18.3 | |
| erlotinib + I-3 | 98.1 | 1.7 | 0.1 | 0.1 | 0.507 |
| Gefitinib + I-3 | 98.1 | 1.5 | 0.2 | 0.2 | 0.100 |
| Imatinib + I-3 | 89.2 | 7.5 | 1.5 | 1.9 | 0.448 |
| Doxorubicin + I-3 | 52.1 | 22.0 | 9.7 | 16.5 | 0.204 |

As shown in Tables 2 to 6, the combination treatment of the compound of the present invention and the existing anti-cancer drugs exhibited strong synergism by obtaining the values of CI ranging from 0.100 to 0.755, as compared with the treatment of only one drug.

As presented in the Experiment Examples, the apoptosis of lung cancer cells (A549) were confirmed by monitoring early apoptosis (AV+/PI−) and total AV+[Sum of early apoptosis (AV+/PI−) and late apoptosis (AV+/PI+)]. The results are shown in Table 7.

TABLE 7

|  | AV+/PI− | CI | Total AV+ | CI |
|---|---|---|---|---|
| Control Group | 1.22 | | 5.18 | |
| I-2 (2.5 μM) | 2.4 | | 6.08 | |
| I-2 (5 μM) | 1.88 | | 4.78 | |
| I-2 (10 μM) | 8.8 | | 13.14 | |
| Etoposide (50 μM) | 19.1 | | 31.68 | |
| Etoposide (50 μM) + I-2 (2.5M) | 25.14 | 0.773 | 37.52 | 0.766 |
| Etoposide (50 μM) + I-2 (5M) | 29.48 | 0.671 | 45.18 | 0.545 |
| Etoposide (50 μM) + I-2 (10M) | 49.06 | 0.342 | 61.96 | 0.257 |

As shown Table 7, Etoposide exhibited synergism in terms of apoptosis induction increase, dependent to the concentration of the compound of the present invention.

The invention claimed is:

1. A 3,4-dihydroquinazoline compound of the following formula (I) or a pharmaceutically acceptable salt thereof:

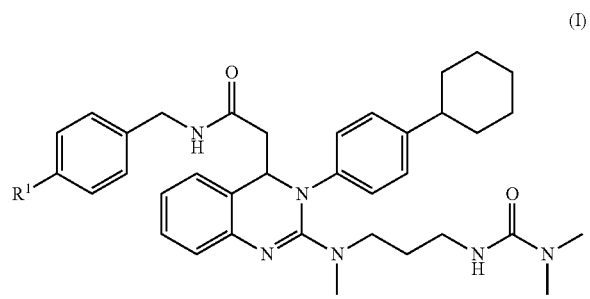

(I)

wherein, $R^1$ is hydrogen, halogen or $C_1$-$C_6$ alkoxy.

2. The 3,4-dihydroquinazoline compound or a pharmaceutically acceptable salt thereof according to claim 1, wherein $R^1$ is halogen or $C_1$-$C_6$ alkoxy.

3. The 3,4-dihydroquinazoline compound or a pharmaceutically acceptable salt thereof according to claim 1, which is selected from the group consisting of:

4-(N-benzylacetamido)-3-(4-cyclohexylphenyl)-2-[N—(N',N'-dimethylureidopropyl)-N-methyl]amino-3,4-dihydroquinazoline (I-1);

4-[N-(4-fluorobenzyl)acetamido]-3-(4-cyclohexylphenyl)-2-[N—(N',N'-dimethylureidopropyl)-N-methyl]amino-3,4-dihydroquinazoline (I-2); and 4-[N-(4-methoxybenzyl)acetamido]-3-(4-cyclohexylphenyl)-2-[N—(N',N'-dimethylureidopropyl)-N-methyl]amino-3,4-dihydroquinazoline (I-3).

4. A composition comprising:
the 3,4-dihydroquinazoline derivative or a pharmaceutically acceptable salt thereof according to claim 1, and
an other anti-cancer drug selected from the group consisting of platinum coordination complexes for antitumor, anthracyclines, topoisomerase inhibitors and tyrosine kinase inhibitors.

5. The composition according to claim 4, wherein the other anti-cancer drug is a platinum coordination complex.

6. The composition according to claim 5, wherein the platinum coordination complex is cisplatin.

7. The composition according to claim 4, and wherein the other anti-cancer drug is an anthracycline.

8. The composition according to claim 7, wherein the anthracycline is doxorubicin.

9. The composition according to claim 4, wherein the other anti-cancer drug is a topoisomerase inhibitor.

10. The composition according to claim 9, wherein the topoisomerase inhibitor is etoposide.

11. The composition according to claim 4, wherein the other anti-cancer drug is a tyrosine kinase inhibitor.

12. The composition according to claim 11, wherein the tyrosine kinase inhibitor is erlotinib, gefitinib or imatinib.

13. A method for treating a cancer comprising administering effective amounts of
(i) the 3,4-dihydroquinazoline derivative or a pharmaceutically acceptable salt thereof according to claim 1, and
(ii) an other anti-cancer drug selected from the group consisting of platinum coordination complexes for antitumor, anthracyclines, topoisomerase inhibitors and tyrosine kinase inhibitors to a subject in need thereof, wherein the cancer is lung cancer or pancreatic cancer.

14. The method according to claim 13, wherein the other anti-cancer drug is a platinum coordination complex.

15. The method according to claim 14, wherein the platinum coordination complex is cisplatin.

16. The method according to claim 13, wherein the cancer is lung cancer, and wherein the other anti-cancer drug is an anthracycline.

17. The method according to claim 16, wherein the anthracycline is doxorubicin.

18. The method according to claim 13, wherein the cancer is lung cancer, and wherein the other anti-cancer drug is a topoisomerase inhibitor.

19. The method according to claim 18, wherein the topoisomerase inhibitor is etoposide.

20. The method according to claim 13, wherein the other anti-cancer drug is a tyrosine kinase inhibitor.

21. The method according to claim 20, wherein the tyrosine kinase inhibitor is erlotinib, gefitinib or imatinib.

22. The method according to claim 13, wherein the 3,4-dihydroquinazoline derivative or a pharmaceutically acceptable salt thereof and the other anti-cancer drug are provided as a single formulation.

23. The method according to claim 13, wherein the 3,4-dihydroquinazoline derivative or a pharmaceutically acceptable salt thereof and the other anti-cancer drug are individually formulated and administered simultaneously or sequentially.

24. A method for providing a therapeutic synergy effect to a cancer treatment, said method comprising administering
- an anti-cancer drug selected from the group consisting of platinum coordination complexes for anti-tumor, anthracyclines, topoisomerase inhibitors and tyrosine kinase inhibitors; and
- a synergistically effective amount of the 3,4-dihydroquinazoline derivative or a pharmaceutically acceptable salt thereof according to claim 1,
- to a subject in need thereof, simultaneously or separately,
- wherein the cancer is lung cancer, sarcoma, malignant melanoma, pleural mesothelioma, bladder cancer, prostate cancer, pancreatic cancer, stomach cancer, ovarian cancer, liver cancer, breast cancer, colon cancer, kidney cancer, esophageal cancer, adrenal cancer, salivary gland cancer, head and neck cancer, cervical cancer, mesothelioma, leukemia, or lymphoma; and
- wherein the synergistically effective amount is an amount providing less than 0.9 of combination index against a cancer.

* * * * *